United States Patent
Williams et al.

(10) Patent No.: US 8,696,563 B2
(45) Date of Patent: Apr. 15, 2014

(54) DEVICE AND METHOD FOR ILLUMINATION OF VAGINAL FORNIX WITH URETER LOCATION, ISOLATION AND PROTECTION DURING HYSTERECTOMY PROCEDURE

(75) Inventors: Steven Williams, White Bear Lake, MN (US); Douglas Ott, Macon, GA (US)

(73) Assignee: Lexion Medical, LLC, St. Paul, MN (US)

( * ) Notice: Subject to any disclaimer, the term of this patent is extended or adjusted under 35 U.S.C. 154(b) by 0 days.

(21) Appl. No.: 13/530,293

(22) Filed: Jun. 22, 2012

(65) Prior Publication Data

US 2013/0131459 A1 May 23, 2013

Related U.S. Application Data

(60) Provisional application No. 61/560,899, filed on Nov. 17, 2011.

(51) Int. Cl.
  *A61B 1/32* (2006.01)
(52) U.S. Cl.
  USPC .......................................... 600/245; 600/249
(58) Field of Classification Search
  USPC .................................................. 600/184–246
  See application file for complete search history.

(56) References Cited

U.S. PATENT DOCUMENTS

| | | | |
|---|---|---|---|
| 4,210,133 A | 7/1980 | Castaneda | |
| 5,066,292 A * | 11/1991 | Muller et al. | 606/7 |
| 5,329,938 A | 7/1994 | Lonky | |
| 5,394,863 A | 3/1995 | Sanford et al. | |
| 5,588,949 A | 12/1996 | Taylor et al. | |
| 6,176,824 B1 | 1/2001 | Davis | |
| 6,516,216 B1 | 2/2003 | Fontenot et al. | |
| 7,306,559 B2 | 12/2007 | Williams | |
| 2002/0007111 A1 | 1/2002 | Deckert et al. | |
| 2003/0220542 A1 | 11/2003 | Belson et al. | |
| 2006/0069313 A1 | 3/2006 | Couvillon, Jr. et al. | |
| 2008/0269565 A1 * | 10/2008 | McMahon et al. | 600/203 |
| 2009/0088636 A1 * | 4/2009 | Lau et al. | 600/439 |
| 2010/0076344 A1 | 3/2010 | Kecman | |
| 2010/0106051 A1 | 4/2010 | Bobo, Sr. | |
| 2011/0184272 A1 | 7/2011 | Zeng et al. | |
| 2011/0190689 A1 | 8/2011 | Bennett et al. | |
| 2012/0143210 A1 | 6/2012 | Brecheen et al. | |
| 2012/0323079 A1 | 12/2012 | Bakare et al. | |
| 2012/0330324 A1 | 12/2012 | Sauer | |

FOREIGN PATENT DOCUMENTS

EP    0 865 760    9/1998

* cited by examiner

*Primary Examiner* — Mary Hoffman
*Assistant Examiner* — Christina Negrellirodriguez
(74) *Attorney, Agent, or Firm* — Winthrop & Weinstine, P.A.

(57) ABSTRACT

The present invention comprises devices and methods that, in certain embodiments, provide a lighted cup, ring or cap that comprises a customizable size and fit, for use in hysterectomy procedures, whereby the ring or cup engages the vaginal fornix and is covered by the vaginal cervical tissue. The lighting allows the surgeon to visualize the location of the lighted cup, ring or cap, thereby quickly and accurately identifying the incision site while providing protection of the associated vasculature and the ureters.

4 Claims, 8 Drawing Sheets

DEVICE AND METHOD FOR ILLUMINATION OF VAGINAL FORNIX WITH URETER LOCATION, ISOLATION AND PROTECTION DURING HYSTERECTOMY PROCEDURE

CROSS-REFERENCE TO RELATED APPLICATIONS

The present application claims priority to provisional application No. 61/560,899, filed on Nov. 17, 2011 and entitled "Lighting Apparatus and Method for Ureter Location, Isolation and Protection During Hysterectomy Procedure", the entire contents of which are incorporated herein by reference.

BACKGROUND OF THE INVENTION

1. Field of the Invention

The invention relates to devices and methods for locating, isolating and protecting ureters during hysterectomy procedures, in certain embodiments providing an illuminating cup or ring or cap over which vaginal cervical tissue is positioned.

2. Description of the Related Art

Known methods of removal of the uterus consist of minimally invasive methods such as laparoscopy and robotic laparoscopic methods. See, e.g., U.S. Pat. No. 5,520,698, describing the primary approaches. A problem that arises during removal of the uterus is the close anatomical relationship of vascular and ureteral structures that may be injured. It is known to use a cup or ring that surrounds the cervix and is used to compress upwardly the vaginal cervical tissue juncture to compress and deflect these structures, thereby helping to reduce damage to the ureters and/or the uterine artery. However, current colpotomizer devices and methods fail to enable critical visualization of the location of the colpotomizer device, specifically, the cup ring device. This failure requires surgeons to awkwardly attempt to locate the device by instrument palpation, a process that is inaccurate and time consuming, requiring repetitive reassessment and introduces the unnecessary hazard of a misguided incision. During robotic surgeries due to loss of force feedback (haptics), palpation is either severely reduced or not appreciated and can lead to making improperly placed incisions, resulting in unnecessary patient injury.

In addition, known colpotomy procedures provide a colpotomy cup which comes in standard sizes, e.g., small, medium and large. Such cups often do not provide an optimal fit; the cup selected should just cover the whole cervix. If, for example, the cup is too large, the ureters will be pulled toward the colpotomy incision, placing the ureters and potentially the uterine artery at risk of damage. Standard, non-customized sized cups present an unnecessary risk to the patient in cases where the fit is not optimal.

The present invention overcomes these deficiencies.

BRIEF SUMMARY OF THE INVENTION

The present invention comprises devices and methods that, in certain embodiments, provide a lighted cup, ring or cap that comprises a customizable size and fit, for use in hysterectomy procedures, whereby the ring or cup engages the vaginal fornix and is covered by the vaginal cervical tissue. The lighting allows the surgeon to visualize the location of the lighted cup, ring or cap, thereby quickly and accurately identifying the incision site while providing protection of the associated vasculature and the ureters.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
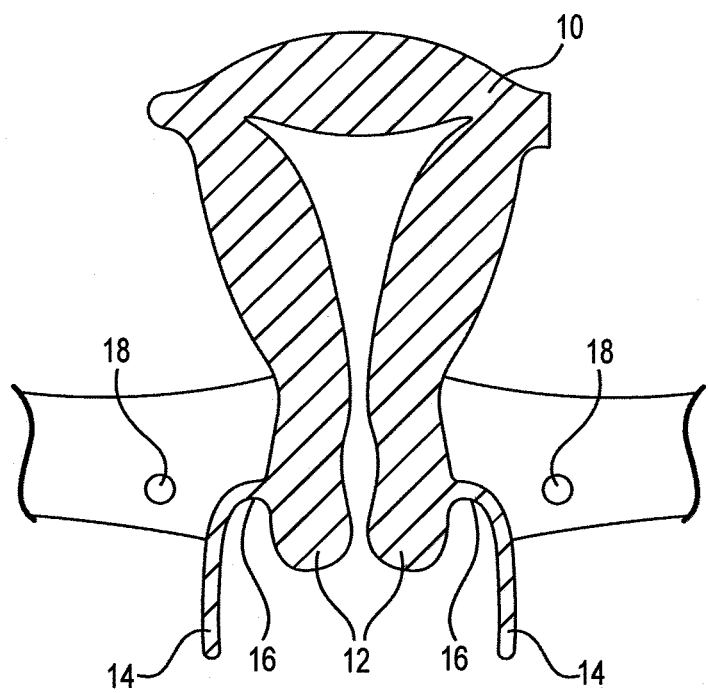
FIG. 1 is a cutaway of the anatomical region of interest.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present invention comprises devices and methods that overcome persistent difficulties in hysterectomy procedures. In various embodiments, a lighted cervical cup comprising lighting elements disposed around the outer lip of the body of the cervical cup is provided. As defined herein "cup" also comprises a cap or ring which are lighted. The lighting elements are sufficiently bright and of appropriate wavelength to allow penetration of the vaginal cervical tissue covering the lighted cup. This allows visualization of the vaginal cervical tissue through an operating scope or projected by a camera without need for tactile instrument palpation.

Thus, using the present device and method, the surgeon is able to readily and visually, without need for indirect palpation, locate the position of the lighted cervical cup. Specifically, the surgeon may readily locate the lighted region of the lighted cervical cup, over which the vaginal cervical tissue is positioned.

Moreover, the known procedures provide a colpotomy cup which comes in conventional sizes, e.g., small, medium and large. Such cups often do not provide an optimal fit; the cup selected should just cover the whole cervix. If, for example, the cup is too large, the ureters will be pulled toward the colpotomy incision, placing the ureters and potentially the uterine artery at risk of damage. Conventional, non-customized sized cups present an unnecessary risk to the patient in cases where the fit is not optimal.

Turning now to FIG. 1, illustrates the relevant anatomy comprising uterus 10, cervix 12, vaginal fornix 14 and the apex 16 of vaginal fornix 14. Ureters 18 are located along essentially the same plane as apex 16. Extreme care must be taken to not damage the ureters 18 during the hysterectomy procedure. This is one of the primary reasons for the present invention: provision of a highly accurate landmarking tool that does not require palpation in order to assist the surgeon in accurately locating the fornix and making accurate incisions while preventing damage to the ureters 18 as well as the uterine artery.

Figure 2:
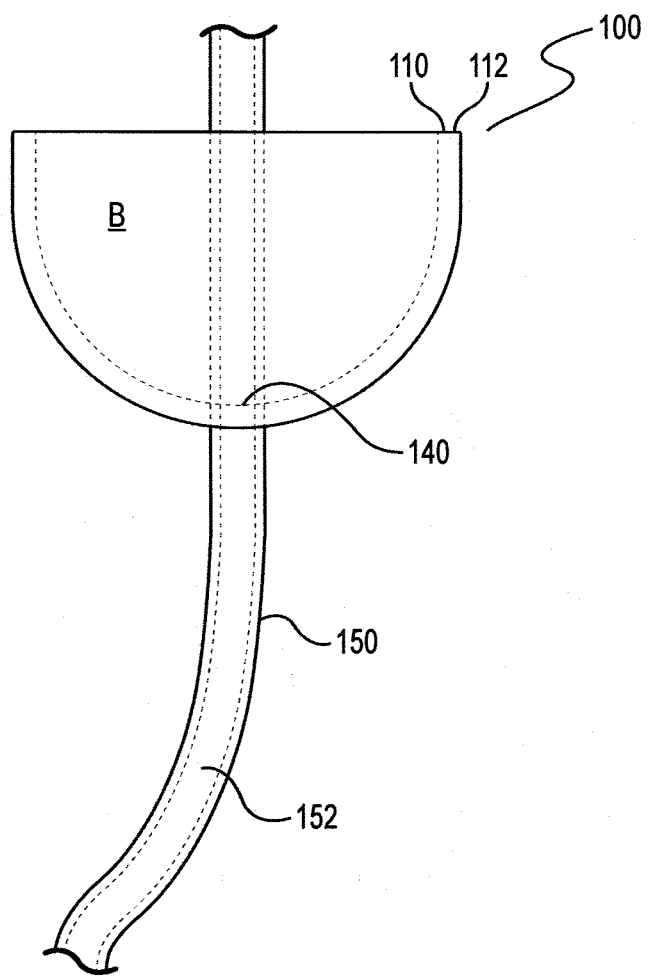
FIG. 2 illustrates one embodiment of the present invention.
Figure 3:
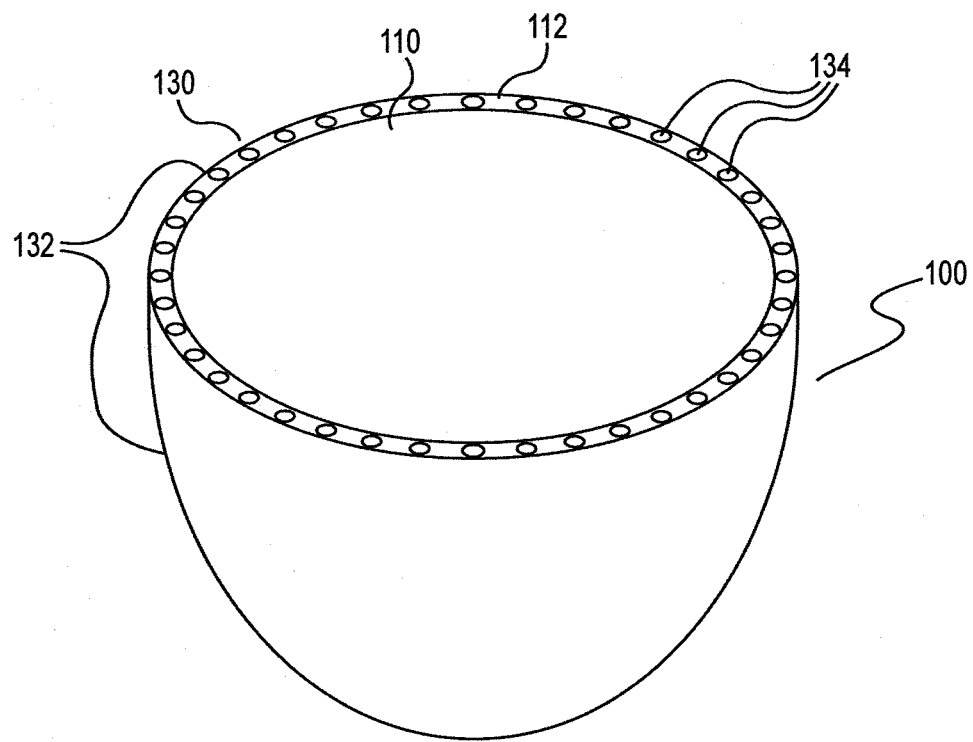
FIG. 3 is a perspective view of one embodiment of the present invention.
Figure 4:
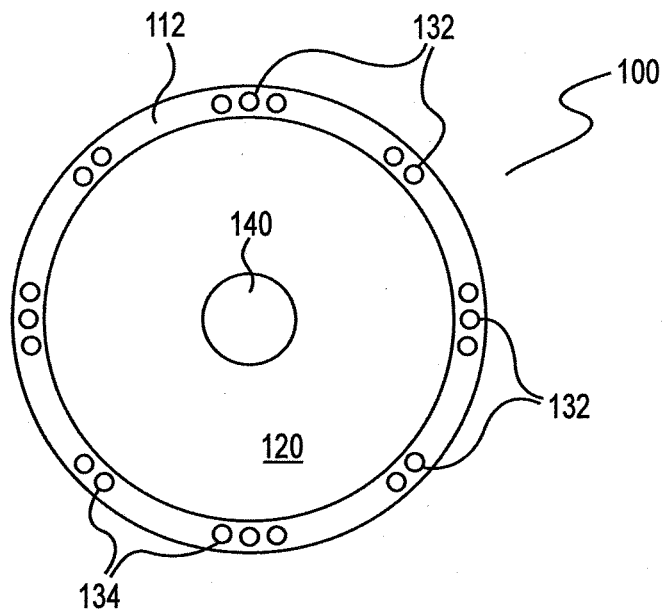
FIG. 4 is a top view of one embodiment of the present invention.

FIGS. 2-4 illustrate certain embodiments of the present invention. Generally, in each embodiment, the lighted cervical cup 100 comprises a body B comprising a rim 110 having an outer lip 112. The cup 100 is formed with a hollow space 120 therein to receive the cervix 12 and the rim 110 is designed to fit within and against the vaginal fornix 14. As illustrated, the lighted cervical cup 100 comprises a spherical shaped profile with approximately one half of the sphere removed. The skilled artisan will recognize that any shaping of the lighted cervical cup 100 will work, e.g., an ellipsoidal shape, as long as the lighted cervical cup 100 receives the cervix 12 and the rim 110 well fits within and against apex 16 of fornix 14. Each such shape is within the scope of the present invention.

FIGS. 2 and 4 illustrate central aperture 140 through lighted cervical cup 100, not shown in FIG. 3, which, when applied to the patient's cervical region and positioned with rim 110 against the apex 16 of fornix 14, allows the surgeon to insert instrumentation therethrough to execute the procedure. Central aperture 140 may be in fluid communication with insertion catheter 150 comprising a lumen 152 therethrough. Insertion catheter 150 may be used to facilitate insertion, positioning and movement of the lighted cervical cup 100 within patient as well as provide a passage for instrumentation to the surgical area.

The embodiment of FIG. 3 illustrates an exemplary lighting structure 130 defining a radial lighting pattern 132 disposed on the outer lip 112 of the rim 110. As illustrated, a plurality of lights 134 comprise a regular lighting pattern 132, formed of a continuous series of individual lights 134, wherein each light 134 is equidistant from the two lights adjacent thereto. The type, source and wavelength(s) of the lighting structure 130 and lights 134 thereof is discussed further herein.

The radial lighting pattern 132 may further comprise an irregular pattern wherein each light 134 in the continuous series of lights 134 are necessarily equidistant from each other. In certain embodiments, therefor, an irregular lighting pattern 132 of the present invention may comprise non-equidistant separations between adjacent lights 134 or any combination of equidistant and non-equidistant separations between adjacent lights 134 on the outer lip 112.

FIG. 4 illustrates a top view of one possible exemplary irregular radial lighting patterns 132. FIG. 4 thus illustrates a lighting pattern 132 comprising a combination of 4 regularly spaced pairs of lights 134 with regularly spaced triplets of lights 134 therebetween. The skilled artisan will readily recognize additional irregular lighting patterns 132, each of which is within the scope of the present invention.

In an alternate embodiment, the radial lighting structure 130 may comprise one solid light 134 around the outer lip 112.

Moreover, during the hysterectomy procedure the surgeon viewing the surgical area laparoscopically and, therefore, is looking down on the internal side of the vaginal fornix while the lighted cup of the present invention is on the other side of the vaginal fornix tissue. Thus, the lighted cup is illuminating the tissue of the vaginal fornix. Therefore, the surgeon is highly dependent on the quality of the surgical light and, when used, the imaging system, to relay information on the health of the tissue as well as its general appearance. Due to the high attenuation of visible light in biological tissue, the quality of the light delivery system to facilitate accurate location of the vaginal fornix, is of utmost importance.

One possible lighting source for the present invention is the xenon arc lamp, which emits over a broad spectrum across the visible range, providing a color close to daylight. Alternative sources of light for the present invention comprise laser-phosphor fibers and supercontinuum lasers. Generally, certain embodiments of the present invention may comprise a lighting structure 130 that may utilize all wavelengths of the visible light spectrum while other embodiments may use certain subsets of the wavelengths comprising the visible light spectrum.

For example, another possible light source for the present invention comprises at least one LED series which may use all wavelengths of the visible light spectrum in certain embodiments. In other embodiments, the at least one LED series may comprise 4 LED's: 1 LED in the red, 1 LED in the green, 1 LED in the blue and 1 LED in the violet ($\lambda<430$ nm) spectral regions. Each LED in the LED series comprise relative intensities that may be adjusted to provide varying levels of white or colored illumination which may be used to provide greater levels of visual detail to the surgeon. In this embodiment, as in others discussed herein, more than one wavelength may be employed to enhance and optimize the visual clarity and detail during the operative procedure. In other embodiments, the at least one LED series may comprise LED's from any wavelength in the visible spectrum and may, therefore, be customized to the individual preference of the surgeon to maximize visibility during the surgical procedure, wherein each LED in the series may comprise or illuminate a different visible light wavelength, or various combinations thereof to maximize visibility. Such combination(s) of wave lengths of light energy may be used individually, or in various combinations, to achieve the desired detail for providing necessary landmarking functionality as well as the visual annunciation of the rim of the cup and the vaginal fornix location.

Alternatively, the lighting structure 130 may be illuminated by a using, e.g., the well-known glowstick chemistry to generate light. In addition, the light selected for the lighting structure may be externally provided to the cup, e.g., an external light tube and/or optical fibers, or may be provided by a source internal to and/or integrated with the lighting structure such as the previously discussed chemically induced light or by on-board batteries and the like. In other embodiments, the lighting structure 130 may be illuminated with infrared and/or ultraviolet light, with visualization using infrared and/or ultraviolet light detector devices which are well known to the skilled artisan.

In further embodiments, the lighting structure 130 may comprise lights 134 that are continually on once actuated. Alternatively, the lights 134 may be on intermittently, or blink, once actuated.

Figure 5:
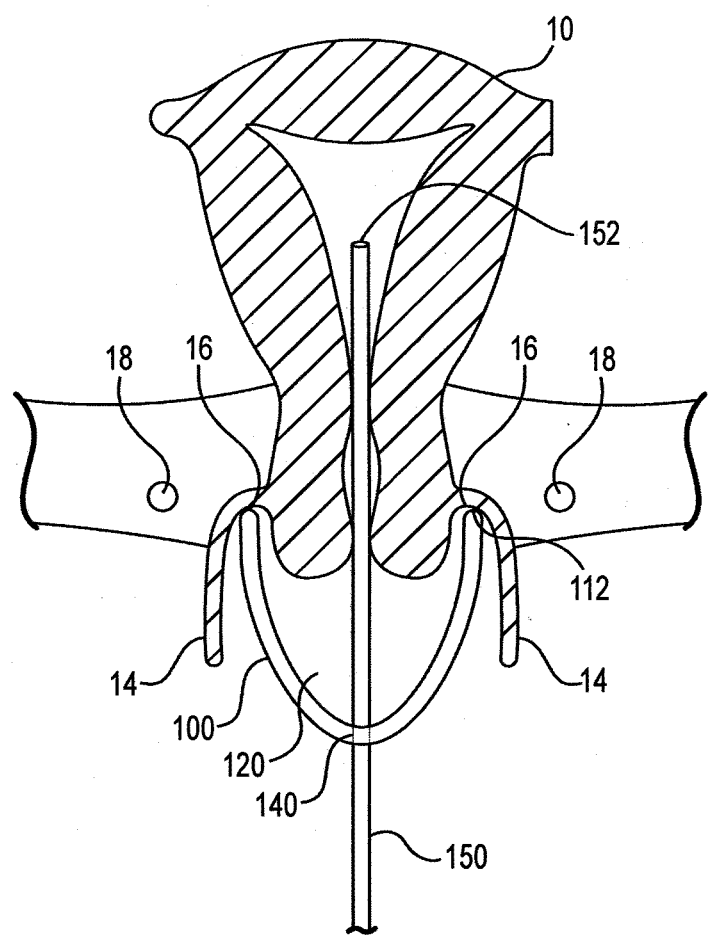
FIG. 5 illustrates one embodiment of he present invention.

FIG. 5 illustrates one embodiment of the present invention wherein the lighted cervical cup 100 is positioned with rim 100 and outer lip 112 comprising lighting structure 130 engaging the patient's fornix 14, specifically the apex 16 thereof. Cervix 12 is received within the hollow 120 of cup 100 and catheter 150 extending through aperture 140 and into uterus 10.

When the lighted cervical cup 100 is positioned as in FIG. 5, such that the cervix 12 is received within the hollow 120 and the rim 100 is positioned against the vaginal fornix apex 16, the surgeon may then optionally, using insertion catheter 150 or, alternatively, an extension device such as that disclosed, e.g., in U.S. Pat. No. 5,520,698, incorporated herein by reference, elevate or extend the vaginal fornix 14 generally toward the patient's head. This movement elevates the uterine artery in relation to the ureters 18 and creates a safe separation between the uterine artery and the ureters 18. The lighting structure 130 allows the surgeon to view the tissue overlaying the cup's outer lip 112 so that appropriate landmarks are identified and accurate and precise incisions may be executed.

Figure 5A:
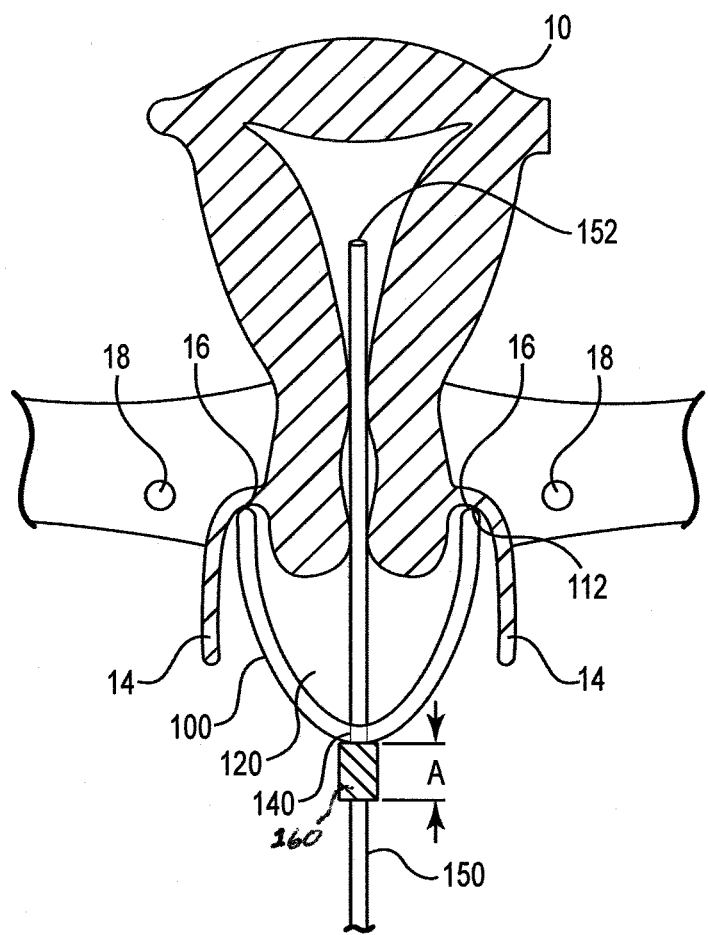
FIG. 5A illustrates one embodiment of the present invention.
Figure 5B:
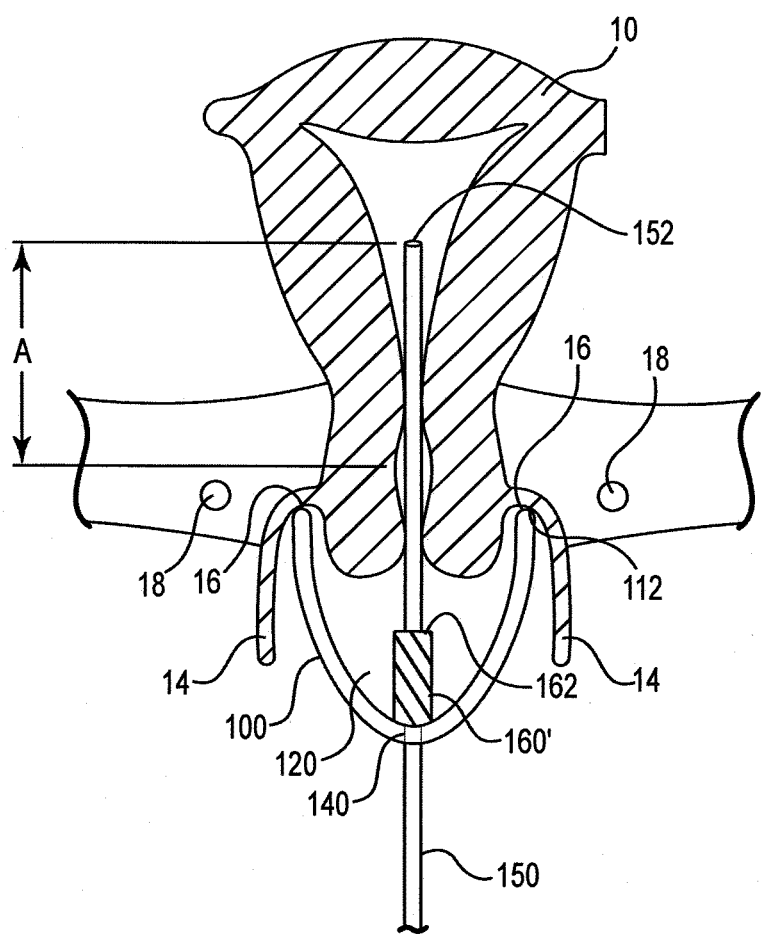
FIG. 5B illustrates one embodiment of the present invention.

FIGS. 5A and 5B illustrate alternate embodiments of the lighted cervical cup 100 fitting neatly within apex 16 as shown in FIG. 5. FIG. 5A provides an actuation device in the form of a pressure sensor switch 160 in combination and operative communication with a power source as is well known in the art and which is in operative communication with the lights 134 in lighting structure 130 and, therefore, when actuated, pressure sensor switch 160 causes the lights 134 to change status, e.g., illuminate constantly or blinkingly illuminate, including the ability to modify the spacing between illuminations by modifying the duty cycle or pulse width of the lights 134, or illuminate in a varying wavelength. Each of the variations in illumination of lights 134 are fully controllable by the operator. In the illustrated embodiment, pressure sensor 160 is attached to catheter 150 at a measured distance from a distal end D of the catheter and cup 100. Once the cup 100 is engaged in apex 16 as discussed above, the operator may apply a sufficient amount of pressure to the catheter 150 so as to engage the pressure sensor switch 160 against the cup 100. The pressure sensor 160 may be actuated through a distance A, and any variation thereof, in order to actuate the lights 134 and lighting structure 130. Thus, a slight pressure may move the pressure sensor 160 a small distance which corresponds to a certain lighting effect. Moving the pressure sensor 160 slightly further may correspond to a different lighting effect. Thus, the distance moved A by pressure sensor switch 160 corresponds with certain lighting effects which are known to and controllable by the operator. Such lighting effects may include, but are not limited to: continuously on for some, or all, lights 134; some, or all, lights 134 blinking in illumination; some or all lights 134 visible in certain wavelengths of the visible, ultraviolet and/or infrared light spectrums; some or all lights 134 visible to an infrared and/or ultraviolet light detector; modification of the blinking illumination cycle for some or all lights 134. The skilled artisan will recognize that a wide variety of lighting effects are possible, each such possibility is within the scope of the present invention.

FIG. 5A illustrates a pressure sensor switch 160 disposed on the exterior of the cup 100, so that the pressure sensor switch 160 engages the bottom surface of the cup 100 to produce the variable lighting effects discussed above. FIG. 5B illustrates an alternative arrangement whereby a pressure sensor switch 160' as discussed above is located within the cup 100 and disposed thereon with an aperture therethrough to allow the sliding passage of catheter 150 once the cup 100 is positioned at apex 16. As the tip of catheter 150 passes through pressure sensor switch 160', the lights 134 are actuated to achieve one of the variety of lighting effects discussed above. The lighting effects may, as above, be correspondent to a distance A' traveled through sensor switch 160' aperture 162.

As further illustrated in FIGS. 5, 5A and 5B the lighted cervical cup 100 fits neatly and comfortably within the fornix' apex 16. Thus, there is no stretching or pulling of the surrounding tissue and, as a result, no distortion of the relative positions of the relevant anatomy, e.g., the positions of the ureters 18 and/or uterine artery. However, in known colpotomy cups, an optimal fit between the cup and the apex 16 is not always achieved, resulting in movement or distortion of the positions of the relevant anatomy, presenting a risk of injury to the patient.

In response, various embodiments of the lighted cervical cup of the present invention may comprise a first retracted position wherein the lighted cervical cup comprises a first retracted position, comprising an essentially cylindrical, and low, profile and a second expanded position, wherein the lighted cervical cup expands to custom fit against and within the patient's anatomy, allowing in certain embodiments to accommodate for and adjust to local variations in radius of the patient's fornix and apex of the fornix.

Figure 6:
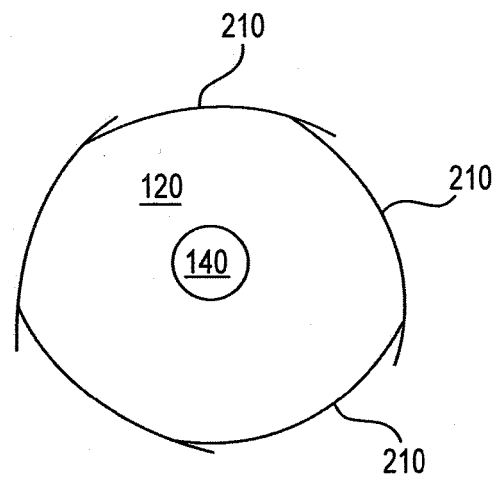
FIG. 6 is a top view of one embodiment of the present invention.
Figure 7:
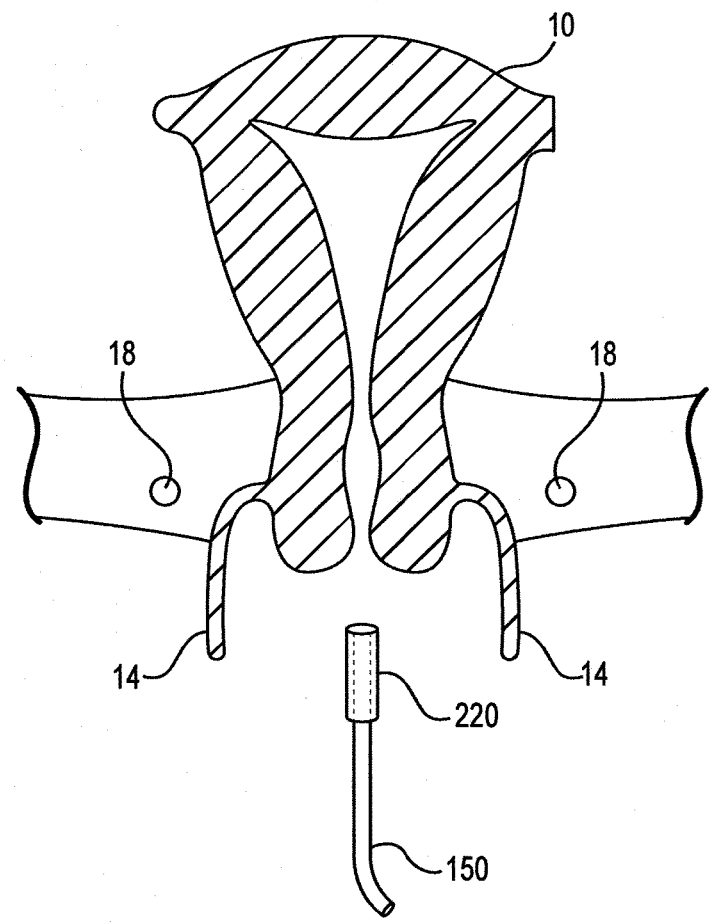
FIG. 7 illustrates one embodiment of the present invention.
Figure 8:
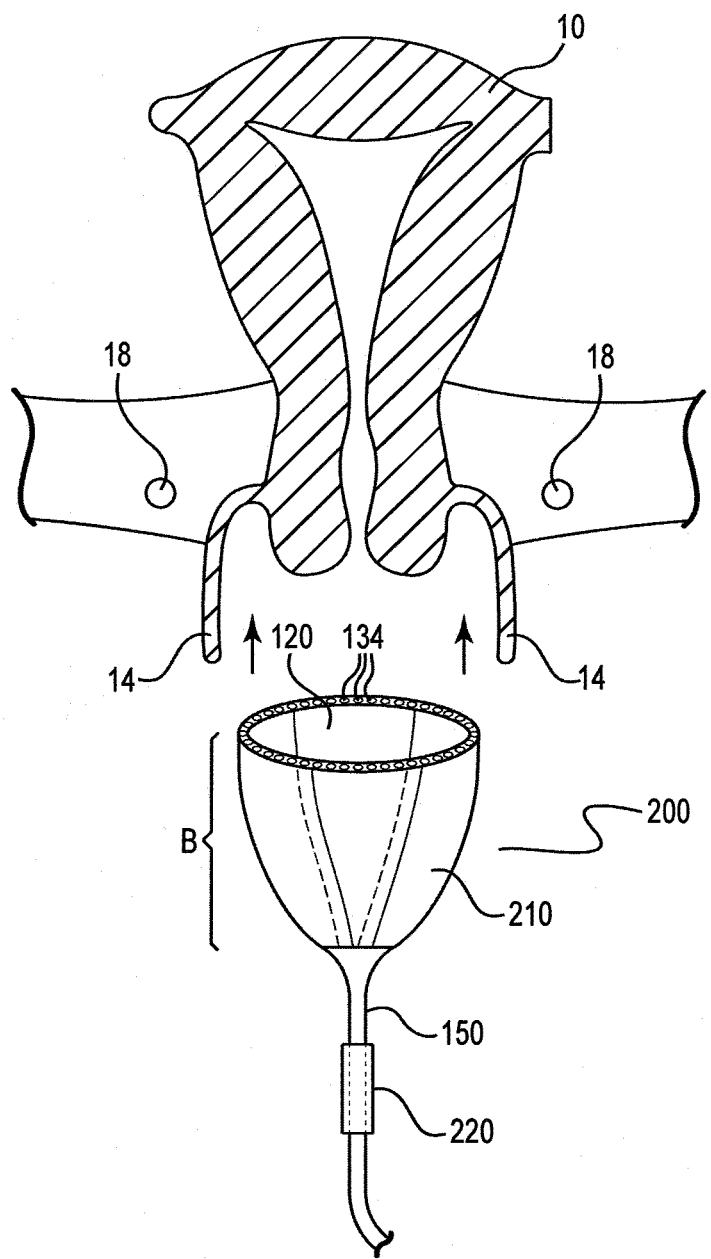
FIG. 8 illustrates one embodiment of the present invention.

The retractable lighted cervical cup 200 may comprise in certain embodiments a body B' formed of a plurality of radiused overlapping leaves or coils 210 which allow contraction of the retractable lighted cervical cup 200 to a first retracted position and expansion to a second expanded position as illustrated in FIGS. 6-8 and with continued reference to FIGS. 1-5. In the illustrated embodiment, the expanded position comprises a conical profile wherein the plurality of overlapping leaves or coils 210 are attached at a hinged base to the end of catheter 150. Each radiused overlapping leaf or coil 210 may slide over the adjacent leaves or coils 210 to expand or collapse the device. Thus, retractable lighted cervical cup 200 is thereby capable of collapsing and winding a small cylindrical diameter within lumen of small diameter sheath 220 in the retracted position and unwinding and expanding to achieve an expanded position. FIG. 6 illustrates a top view of one embodiment of the retractable lighted cervical cup 200 in a second expanded position.

In practice the retractable lighted cervical cup 200 is in the first retracted position when inserted into the patient's vaginal cavity and when adjacent the patient's fornix 14 and, in preparation for receiving the cervix within the hollow 120', expanded to achieve a second expanded position. Such movement between the first retracted position to the second expanded position may be actuated by a wire connecting each of the overlapping leaves controlled by the surgeon as is known in the art. Equivalent structures for moving from a retracted to an expanded position will readily present themselves to the skilled artisan. Each such structure is within the scope of the present invention.

Further, the retracted first position may comprise a deformed position, wherein the retractable lighted cervical cup 200 is biased to the second expanded position. In such an embodiment, the cup or ring will, when released from the first retracted position, automatically move to the expanded second position. For example, and without limitation, the overlapping leaf embodiment may comprise one or more springs connecting the overlapping leaves and which provide a biasing force which tends to move the cup 200 to the expanded second position.

The biasing force may be overcome by drawing the small diameter base of the conically profiled cup 200 into the lumen of a small diameter sheath, thereby causing the leaves to overlap, winding around each other and to collapse, placing the cup 200 in a substantially cylindrical profile, i.e., into the first retracted position. The lighted cup 200 may be biasingly expanded to achieve the second expanded position by releasing the lighted cup 200 from the confines of the sheath's lumen, thereby enabling the cup or ring to automatically biasingly achieve the second expanded position. The overlapping radiused leaves 210 thus exert a slight biasing force outwardly, causing the individual leaves 210 against the patient's anatomy. As a result of this configuration, the retractable lighted cervical cup 200 may achieve a plurality of second expanded positions, dependent upon the anatomical configuration encountered, thereby increasing the accuracy and safety of the procedure.

One advantage of the configuration comprising a plurality of biased second expanded positions which the retractable lighted cervical cup 200 achieves automatically is that the retractable lighted cervical cup 200 will only expand to the point at which the biasing force is again overcome. This allows the cup 200 to expand to precisely fit within the fornix apex 16, thereby achieving a custom fit for each vaginal fornix 14 dimension when the apex 16 of the fornix 14 is engaged by the retractable lighted cervical cup 200. As discussed above, this customized fitting of the cup 200 with the fornix apex 16 allows the relevant anatomy to remain in position, without movement or distortion caused by an ill-fitting cup 200.

Alternatively, the retractable lighted cervical cup 200 may, in other embodiments, comprise a shape memory alloy wherein the change from the first retracted position to the second expanded position occurs upon exposure to a body temperature. A preferred shape memory alloy comprises Nitinol. Similar to the mechanically biased embodiment discussed supra, the shape memory embodiments may also comprise an automatic custom fit ability, whereby the retractable lighted cervical cup 200 is biased to the second expanded position upon exposure to body temperature, but when the cup or ring expands to encounter the anatomical wall, the biasing force of the shape memory alloy, e.g., Nitinol, is overcome and expansion stops. Thus, the cup 200 may automatically provide an expansion custom fit for all vaginal dimensions, allowing for a custom fit for the cup into the apex 16 of the fornix 14. In this embodiment, the cup 200 may be formed of overlapping leaves or a basket or similar structure.

When the hysterectomy procedure is complete, the surgeon may either pull the retractable lighted cervical cup 200 distally or back toward the sheath, engaging the smaller diameter portion 18 of the retractable cup, thus causing the expanded cervical cup to collapse and retract within the sheath's lumen 30. When fully retracted, the flexible shaft 26 and retracted cutting element may be withdrawn from the patient.

Thus, a method of using the present invention to position a lighted cervical cup for a hysterectomy procedure may comprise:

providing a retractable lighted cervical cup 200 capable of actuatingly moving from a first retracted position to a second expanded position;

advancing the retractable lighted cervical cup 200 into the patient's vaginal cavity to a position proximate the fornix;

actuating the retractable lighted cervical cup 200 to an expanded position;

positioning the retractable lighted cervical cup 200 within the patient's fornix, specifically, providing a custom fitting of the rim and outer lip of the cup 200 within the apex of the patient's fornix;

executing and completing the hysterectomy procedure with or without cervical removal;

actuating the retractable lighted cervical cup 200 back into the first retracted position; and withdrawing the retractable lighted cervical cup 200 from the patient.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for using a lighted cervical cup in a hysterectomy procedure comprising:

providing a lighted cervical cup with a lighting structure comprising lights mounted around an outer rim of the cup;

advancing the lighted cervical cup into the patient's vaginal cavity to a position proximate the vaginal fornix;

actuating at least one of the lights of the lighting structure to achieve one of a plurality of lighting effects;

positioning the lighted cervical cup within the patient's fornix, specifically, thereby fitting the rim and an outer lip of the cup within the apex of the patient's fornix;

viewing the lighting effect achieved for maximum visibility of the patient's tissue and modifying the lighting effect by actuating at least one of the lights of the lighting structure to improve visibility if necessary;

executing and completing the hysterectomy procedure; and withdrawing the lighted cervical cup from the patient.

2. The method of claim 1, further comprising providing one of the group consisting of a light tube, optical fibers, and chemical induction; and illuminating the lighting structure with one of the group consisting of the light tube, the optical fibers and the chemical induction.

3. The method of claim 1, further comprising providing a pressure sensor switch disposed on the catheter and in operable communication with a power source and the lighting structure; and actuating at least one of the lights with the pressure sensor switch to achieve the lighting effect.

4. The method of claim 1, wherein the lighting structure comprises at least one LED light series in the visible wavelengths, the at least one LED light series consisting of 1 LED light in the red spectral region, 1 LED light in the green spectral region, 1 LED light in the blue spectral region and 1 LED light in the violet spectral region.

* * * * *